United States Patent
Ma et al.

(10) Patent No.: US 10,256,516 B2
(45) Date of Patent: Apr. 9, 2019

(54) STABLE ELECTROLYTE FOR LITHIUM AIR BATTERY AND LITHIUM AIR BATTERY INCLUDING THE SAME

(71) Applicants: Samsung Electronics Co., Ltd., Suwon-si, Gyeonggi-do (KR); Massachusetts Institute of Technology, Cambridge, MA (US)

(72) Inventors: Sang Bok Ma, Cambridge, MA (US); Mariya Khiterer, Cambridge, MA (US); Young-Gyoon Ryu, Lexington, MA (US); Paula T. Hammond, Newton, MA (US); Yang Shao-Horn, Newton, MA (US); Chibueze Vincent Amanchukwu, Richmond, TX (US)

(73) Assignees: SAMSUNG ELECTRONICS CO., LTD., Gyeonggi-Do (KR); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 604 days.

(21) Appl. No.: 14/949,498

(22) Filed: Nov. 23, 2015

(65) Prior Publication Data
US 2017/0149104 A1 May 25, 2017

(51) Int. Cl.
| | |
|---|---|
| *H01M 10/056* | (2010.01) |
| *H01M 12/08* | (2006.01) |
| *C07C 309/01* | (2006.01) |
| *C07C 311/48* | (2006.01) |
| *H01M 4/38* | (2006.01) |
| *H01M 4/587* | (2010.01) |
| *H01M 8/0204* | (2016.01) |
| *H01M 10/0525* | (2010.01) |
| *H01M 10/0567* | (2010.01) |
| *H01M 4/02* | (2006.01) |

(52) U.S. Cl.
CPC ........... *H01M 12/08* (2013.01); *C07C 309/01* (2013.01); *C07C 311/48* (2013.01); *H01M 4/38* (2013.01); *H01M 4/587* (2013.01); *H01M 8/0204* (2013.01); *H01M 10/0525* (2013.01); *H01M 10/0567* (2013.01); *H01M 2004/027* (2013.01); *Y02E 60/128* (2013.01)

(58) Field of Classification Search
CPC ......... H01M 10/0525; H01M 10/0567; H01M 4/38; H01M 4/587; C07C 311/48; C07C 309/00
See application file for complete search history.

(56) References Cited

U.S. PATENT DOCUMENTS

| | | | |
|---|---|---|---|
| 2002/0076619 A1 | 6/2002 | Yamada et al. | |
| 2013/0045428 A1 | 2/2013 | Visco et al. | |
| 2013/0131201 A1 | 5/2013 | Goldbach et al. | |
| 2014/0106240 A1* | 4/2014 | Kotani | H01M 4/50 429/405 |

OTHER PUBLICATIONS

A.S. Shaplov, D.O. Ponkratov, P.S. Vlasov, E.I. Lozinskaya, I.A. Malyshkina, F. Vidal, P. -H. Aubert, M. Armand, and Ya. S. Vygodskii, Solid-State Electrolytes Based on Ionic Network Polymers, Polymer Science, Ser. B, 2014, vol. 56, No. 2, pp. 164-177.*

* cited by examiner

*Primary Examiner* — Ula C Ruddock
*Assistant Examiner* — Thomas H. Parsons
(74) *Attorney, Agent, or Firm* — Cantor Colburn LLP

(57) ABSTRACT

Provided are electrochemical cells that include a compound having the general formula

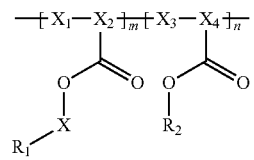

wherein $R_1$ is moiety associated with a lithium ion, $X_1$ and $X_3$ are unsubstituted methylene moieties, $X_2$ and $X_4$ are each independently selected from a substituted or unsubstituted methylene moiety, X is a substituted or unsubstituted $C_1$-$C_{10}$ alkylene moiety, arylene moiety or heteroarylene moiety, $R_2$ is selected from Li, H, an alkyl moiety, or a heteroalkyl moiety, $0 < m \le 1$, $0 \le n \le 1$, and $m+n=1$.

25 Claims, No Drawings

STABLE ELECTROLYTE FOR LITHIUM AIR BATTERY AND LITHIUM AIR BATTERY INCLUDING THE SAME

TECHNICAL FIELD

Disclosed are electrochemical cells that contain a stable polyacrylate electrolyte compound described herein that may be suitable for energy storage applications, e.g., for batteries that employ Li—$O_2$ electrochemistry.

BACKGROUND

In general, there is a need for lithium-based, lithium-ion based, or similar electrochemical cells that exhibit high energy density over a large number of charge-discharge cycles. There are two basic approaches to achieve high energy density in such cells. The first involves providing high energy materials. The second involves using light-weight materials.

For example, the first approach may involve providing anode and cathode materials that exhibit a high electrochemical potential difference. This approach typically requires the use of an electrolyte containing lithium ions that is substantially electrochemically stable relative to both the anode and the cathode. This approach also typically involves the formation of an ionically conductive layer that allows for appropriate electrochemistry to take place without unwanted side reactions. Optionally, the electrolyte may be provided in the form of catholyte, a material that is considered both a cathode material and an electrolyte material.

As discussed above, the second approach to achieve high energy density involves providing lightweight electrode materials. Accordingly, the large free energy of the reaction between lithium metal and air has attracted the interest of battery researchers for decades. Both lithium metal and air are considered light-weight materials. At a nominal potential of about 3 volts, the theoretical specific energy for a Li/$O_2$ battery in a non-aqueous electrolyte is over 11,000 Wh/kg for the reaction forming $Li_2O_2$. Such a battery would rival the energy density for hydrocarbon fuel cells. Some have suggested that rechargeable Li/Air cells and batteries could be commercially viable if lithium containing anodes were protected in a manner to ensure that moisture in air does not directly contact the lithium therein so as to avoid generating hydrogen gas in an uncontrolled manner.

In short, there is a need to provide novel and nonobvious materials to address the above-discussed technical problems. There is also a need to provide an electrochemical cell of an appropriate construction to meet the long-felt need for stable and high-performance electrochemical batteries that exhibit exceptional high energy density.

SUMMARY OF THE INVENTION

In general, the invention relates to an electrochemical cell that includes negative and positive electrodes, an electrolyte in electrochemical contact with the electrodes, and a container containing electrodes and the electrolyte. The cell also may also include a compound having the formula

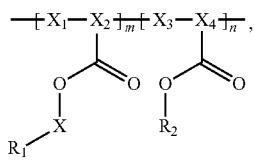

wherein
$R_1$ has a formula selected from

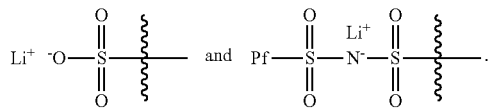

Typically, $X_1$ and $X_3$ are unsubstituted methylene moieties, $X_2$ and $X_4$ are each independently selected from a substituted or unsubstituted methylene moiety, and X is a substituted or unsubstituted $C_1$-$C_{10}$ alkylene moiety, arylene moiety or heteroarylene moiety. Also typically, Pf is $C_1$-$C_{10}$ alkyl moiety, $R_2$ is selected from Li, H, an alkyl moiety, or a heteroalkyl moiety, 0<m≤1, 0≤n≤1, and m+n=1. The compound may have an average molecular weight of about 1000 g/mol to about 1,000,000 g/mol. From a chemical and/or electrochemical sense, the compound is considered stable.

For example, the invention may take the form of an alkali metal/air cell that includes the above-identified compound. The alkali metal, for example, may be lithium, sodium or potassium.

DETAILED DESCRIPTION OF THE INVENTION

Overview and Definitions

The invention provides useful, novel and nonobvious electrochemical cells that include a chemical compound having a formula as generally described herein. The compound may include a moiety associated with a lithium ion, which may be dissociated upon interaction with a negative ion and/or upon application of an electrical potential Before describing the invention in detail, it is to be understood that this invention, unless specifically noted to the contrary, is not limited to any particular cells, batteries, electrically powered device, or the like, as such may vary. In addition, numerous electrochemical cell configurations may be used to form embodiments described herein. It is also to be understood that the terminology used herein is for the purpose of describing particular embodiments only, and is not intended to be limiting.

In this specification and in the claims that follow, reference is made to a number of terms that are defined to have the following meanings, unless the context in which they are employed clearly indicates otherwise:

As used herein, the singular forms "a," "an," and "the" include both singular and plural referents unless the context clearly dictates otherwise. Thus, for example, reference to "a battery comprising a cell" includes one or more batteries that may include plurality of cells as well as a single battery consisting of a single cell, reference to "a compound" includes a combination of compounds as well as a compounds, and the like.

The term "and/or" when used in a list of items, refers to the any of the items singly or in combination, unless the context clearly dictates otherwise. For example, "Z1, Z2 and/or Z3" refers to "Z1," "Z2," "Z3," "Z2 and Z3," "Z1 and Z3," "Z2 and Z3," or "Z1, Z2, and Z3," or any permutation of the foregoing.

The terms "anode" and "cathode" are interchangeably used with the terms "negative electrode" and "positive electrode," respectively.

The terms "electronic," "electronically," and the like are used in their ordinary sense and relate to structures, e.g., semiconductor microstructures, that provide controlled conduction of electrons, holes, or other charge carriers.

The term "electrolyte" is used herein to refer a material through which ions may, under an electric potential gradient, diffusion forces, and/or the like, migrate. Electrolytes may be solid, liquid and/or gaseous. Typically, an electrolyte exhibits high ionic conductivity and low electronic conductivity.

The term "moiety" is used in its ordinary chemical sense and refers to a part or functional group of a molecule. Similarly, the terms "substituted," "unsubstituted," "methylene," "$X_2$," "$X_4$," "X," "independently selected," "$C_1$-$C_{10}$," "alkylene," "arylene," "hetero" "$R_1$," "$R_2$," "Li," "H," and the like are to be interpreted in their ordinary chemical sense as well.

The terms "substantial" and "substantially" are used in their ordinary sense and mean "of considerable importance" or "to a great or significant extent," but that trivial or insignificant counterexamples may be found. For example, a "substantially solid-state" battery is to be interpreted to mean a battery comprising entirely or consisting essentially of solid components, but that the battery does not have to exclude components that are entirely devoid of fluids as long as the operation of the battery is not hindered. In addition, a "substantially stable compound" for use in an electrochemical cell may mean a compound that is considered stable electrochemically and/or chemically given the electrochemistry within the cell under ordinary circumstances, but that the compound does not have to be completely stable when exposed to abusive or unintended operational conditions.

The term "solution" is used in its chemical sense and refers to one or more solutes in a solvent. A solution may be fluid or solid in nature. For example, a solid-state solution differs from a solid-state compound in that the crystal structure of the solvent remains unchanged by addition of the solutes and that the solution may remain in a single homogeneous phase.

The term "stable," as in a "stable compound," is generally used in its chemical and/or electrochemical sense and refers to something, e.g., a compound," that is not likely to change, fail, or undergo and undesirable chemical change that renders the invention completely inoperative.

An Exemplary Electrochemical Cell

In general, the invention provides an electrochemical cell in combination with the stable compounds described herein. Any of a number of electrochemical cell constructions may be used. Typically, the inventive cell includes a negative electrode, a positive electrode, and an electrolyte in electrochemical contact with the electrodes. In some instances, an anolyte may be provided that serves as a dual purpose, i.e., as both the anode and electrolyte. Similarly, a catholyte may be provided, in the alternative or in addition, that serves as both the cathode and the electrolyte.

The anode, cathode, and electrolyte are located within a cell container. Depending on the desired chemistry, the container may be sealed or be at least permeable to certain but not other electrochemical reactants. For example, when the invention takes the form of a lithium-air cell, the container may be constructed ensure that potentially undesirable compounds such as water, does not generate uncontrolled hydrogen gas.

A polyacrylate compound having the following general formula may be used.

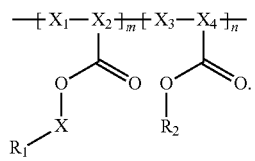

Typically, $R_1$ has a formula selected from

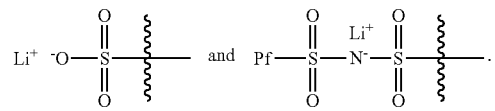

Also typically, $X_1$ and $X_3$ are each an unsubstituted methylene moiety, $X_2$ and $X_4$ are each independently selected from a substituted or unsubstituted methylene moiety, X is a substituted or unsubstituted $C_1$-$C_{10}$ alkylene moiety, arylene moiety or heteroarylene moiety, Pf is $C_1$-$C_{10}$ alkyl moiety, $R_2$ is selected from Li, H, an alkyl moiety, or a heteroalkyl moiety, $0<m\leq1$, $0\leq n\leq1$, and m+n=1, and/or compound has an average molecular weight of about 1000 g/mol to about 1,000,000 g/mol. Optionally, $X_2$ and $X_4$ are selected from $CH_2$, CHF, and $CF_2$, and/or Pf is a $C_1$-$C_{10}$ fluoroalkyl moiety, e.g., a perfluoroalkyl moiety. In some cases, the $Li^+$ ions associated with polyacrylate compound can be substituted with $H^+$, $Na^+$, and/or $K^+$ ions Typical, the compound is located within the cell container. For example, the compound may be located in the electrolyte. In addition or in the alternative, the compound may be located at an interface between the negative electrode and the electrolyte and/or at an interface between the positive electrode and the electrolyte.

In some instances, an interfacial interfacial layer may be formed on an electrode surface by the compound. The interfacial layer may be formed in any of a number of ways. For example, the interfacial layer may be formed upon charging and/or discharging of the cell. In addition or in the alternative, the interfacial layer may be formed upon assembling of the cell and/or upon the filling of the cell container.

The invention may be used with any of different anode materials. For example, the negative electrode may comprise carbon, optionally in a layered form, e.g., as a mesophase or graphitic carbon. In addition or in the alternative, a metallic material, e.g., metallic Li may be used. Optionally, the negative electrode material may be capable of reversible Li insertion and/or intercalation.

The electrolyte may comprise a fluid phase that includes a salt in solution. The fluid phase is more typically substantially aprotic, but electrolyte materials such as polyethylene oxide (PEO, also known as polyethylene glycol with terminal hydroxyl moieties from which H ions may be liberated) may be sparingly used. In any case, the fluid phase typically contains a salt or salt-like moieties that easily, dissociates positive ions such as H, Li, Na, and/or K. However, the electrolyte may, alternatively or additionally, be solid, liquid or gel. In some instances, a ceramic electrolyte may be used. The electrolyte may comprise or consist essentially of the ion-conductive polyacrylate material, as discussed above, which may not exhibit a high electronic conductivity.

The inventive cell typically has an open circuit voltage of at least about 3.0 volts when charged. However higher or lower voltages may occur depending on the specific chemistry involved Numerous alternatives and equivalents exist which do not depart from the invention set forth above. For example, the cathode material may include a substance other than $O_2$. For example, the invention may use a cathode material, the solid electrolyte material, an electronically conductive material and a binder. Cathode active materials suitable for a solid-state lithium battery are typically highly Li-conductive and exhibit a relative high voltage against metallic Li. In contrast, cathode materials may be ionically nonconductive but electronically conductive Microstructurally similar materials used in known Li-ion electrochemical cells may be used here. For example, $FeS_2$, $MnO_2$, spinel $LiMn_2O_4$, $LiCoO_2$, $LiNiO_2$ may serve as electroactive cathode materials. Examples of electronically conductive materials for use in the cathode include acetylene black and graphitic materials. The cathode active material layer may also contain a binder. Exemplary binders include fluorine-containing polymers such as polytetrafluoroethylene (PTFE) and polyvinylidene fluoride (PVDF). Examples of current collector materials for the cathode layer include aluminum, nickel, iron, titanium and carbon.

The anode layer includes an anode material and optionally includes the solid electrolyte material, an electronically conductive material, and a binder material. Examples of the anode materials include but are not limited to metallic Li, alloys thereof, and metal active materials in combination with carbon active material. Examples of anode active material include metals such as In, Al, Si, and Sn. On the other hand, examples of the carbon active material include mesocarbon microbeads (MCMB), high orientation property graphite (HOPG), hard carbon and soft carbon.

The electronically conductive material and a binder used for the anode active material layer may be the same as or similar to those contained in the cathode layer. Exemplary anode current collector materials include copper, nickel and carbon.

Although the examples of embodiments described herein relate to room-temperature batteries, embodiments may be used in elevated temperature environments, e.g., human body temperature or greater. It should be apparent that liquid anode and cathode materials may be used as well.

It is to be understood that, while the invention has been described in conjunction with the preferred specific embodiments thereof, the foregoing description merely illustrates and does not limit the scope of the invention. For example, while the bulk of the disclosure focuses on Li or Li ion chemistry, the invention is not limited to Li batteries. The invention may be adapted for H, Na, or K chemistry. That is, the above-identified polyacylate polymer was tested with respect to $K^+$ ions because neither K nor Li affects the stability of polyacylate structure. Thus, carrier ions such as Li, H, K and Na can be selected according to the battery system of interest, e.g., Li-Air, Na-Air, etc. In addition, the invention may be used to avoid detrimental dendritic growth. Furthermore, when a numerical range is recited, the range is to be interpreted to as if every number within the numerical range is individually recited. Other aspects, advantages, and modifications within the scope of the invention will be apparent to those skilled in the art to which the invention pertains.

All publications, patent applications, and patents mentioned herein are hereby incorporated by reference in their entireties to an extent consistent with the above disclosure.

We claim:
1. An electrochemical cell, comprising:
a cell container, containing therein
 a negative electrode,
 a positive electrode, and
 an electrolyte in electrochemical contact with negative and positive electrodes; and
a compound having the formula

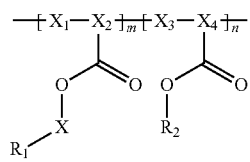

wherein
 $R_1$ has a formula selected from

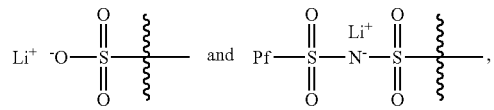

and further wherein
 $X_1$ and $X_3$ are each an unsubstituted methylene moiety,
 $X_2$ and $X_4$ are each independently selected from a substituted or unsubstituted methylene moiety,
 X is a substituted or unsubstituted $C_1$-$C_{10}$ alkylene moiety, arylene moiety or heteroarylene moiety,
 Pf is a substituted or unsubstituted $C_1$-$C_{10}$ alkyl moiety,
 $R_2$ is selected from Li, H, an alkyl moiety, or a heteroalkyl moiety,
 $0<m\le1$, $0\le n\le1$, and $m+n=1$, and
 the compound has an average molecular weight of about 1000 g/mol to about 1,000,000 g/mol.
2. The cell of claim 1, wherein the compound is located in the electrolyte.
3. The cell of claim 1, wherein the compound is located at an interface between the negative electrode and the electrolyte.
4. The cell of claim 1, wherein the compound is located at an interface between the positive electrode and the electrolyte.
5. The cell of claim 1, wherein an interfacial layer is formed on an electrode surface by the compound.
6. The cell of claim 5, wherein the interfacial layer is formed upon charging of the cell.
7. The cell of claim 5, wherein the interfacial layer is formed upon discharging of the cell.
8. The cell of claim 5, wherein the interfacial layer is formed upon assembling of the cell.
9. The cell of claim 5, wherein the interfacial layer is formed upon the filling of the cell container.
10. The cell of claim 1, wherein the negative electrode comprises carbon.
11. The cell of claim 10, wherein the negative electrode comprises a layered form of carbon.
12. The cell of claim 1, wherein the negative electrode comprises a metallic material.
13. The cell of claim 1, wherein the negative electrode comprises a negative electrode material capable of reversible Li insertion.

14. The cell of claim 13, wherein the negative electrode material is capable of reversible Li intercalation.

15. The cell of claim 1, wherein $O_2$ serves as an electroactive material at the positive electrode.

16. The cell of claim 1, wherein the electrolyte consists essentially of the compound in a solid form.

17. The cell of claim 1, having an open circuit voltage of at least about 3.0 volts when charged.

18. The cell of claim 1, $X_2$ and $X_4$ are each independently selected from $CH_2$, CHF, and $CF_2$.

19. The cell of claim 1, wherein Pf is a $C_1$-$C_{10}$ fluoroalkyl moiety.

20. The cell of claim 19, wherein Pf is $C_1$-$C_{10}$ perfluoroalkyl moiety.

21. The cell of claim 1, wherein $0<m<1$ and $0<n<1$.

22. An alkali metal/air cell that includes a compound having the formula

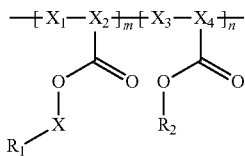

wherein
$R_1$ has a formula selected from

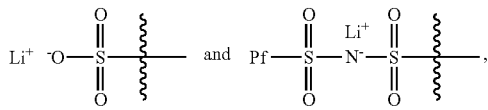

and further wherein
$X_1$ and $X_3$ are each an unsubstituted methylene moiety,
$X_2$ and $X_4$ are each independently selected from a substituted or unsubstituted methylene moiety,
X is a substituted or unsubstituted $C_1$-$C_{10}$ alkylene moiety, arylene moiety or heteroarylene moiety,
Pf is a substituted or unsubstituted $C_1$-$C_{10}$ alkyl moiety,
$R_2$ is selected from Li, H, an alkyl moiety, or a heteroalkyl moiety,
$0<m\leq1$, $0\leq n\leq1$, and m+n=1, and
the compound has an average molecular weight of about 1000 g/mol to about 1,000,000 g/mol.

23. The cell of claim 22, wherein the cell is a lithium air cell.

24. A rechargeable cell, comprising:
an anode for lithium ion insertion and deinsertion;
a cathode comprising oxygen as a cathode active material; and
a lithium ion conductive electrolyte disposed between the anode and the cathode,
wherein the electrolyte comprises a compound having the formula

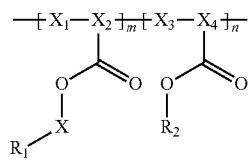

wherein
$R_1$ has a formula selected from

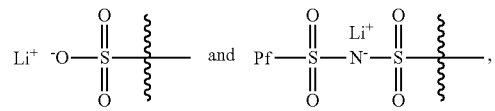

and further wherein
$X_1$ and $X_3$ are each an unsubstituted methylene moiety,
$X_2$ and $X_4$ are each independently selected from a substituted or unsubstituted methylene moiety,
X is a substituted or unsubstituted $C_1$-$C_{10}$ alkylene moiety, arylene moiety or heteroarylene moiety,
Pf is a substituted or unsubstituted $C_1$-$C_{10}$ alkyl moiety,
$R_2$ is selected from Li, H, an alkyl moiety, or a heteroalkyl moiety,
$0<m\leq1$, $0\leq n\leq1$, and m+n=1, and
the compound has an average molecular weight of about 1000 g/mol to about 1,000,000 g/mol.

25. The cell of claim 24, wherein the anode includes an anode active material that is capable of reversibly intercalating lithium ions.

* * * * *